United States Patent
Preisig et al.

(10) Patent No.: US 10,391,061 B2
(45) Date of Patent: *Aug. 27, 2019

(54) DELAYED RELEASE PHARMACEUTICAL FORMULATION AND METHODS OF MAKING AND USING SAME

(71) Applicant: Tillotts Pharma AG, Rheinfelden (CH)

(72) Inventors: Daniel Preisig, Basel (CH); Maxim Puchkov, Pfeffingen (CH); Joerg Huwyler, Arlesheim (CH); Felipe José Oliveira Varum, Basel (CH); Roberto Carlos Bravo Gonzalez, Binningen (CH)

(73) Assignee: Tillotts Pharma AG, Rheinfelden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,146

(22) Filed: Jan. 9, 2018

(65) Prior Publication Data

US 2018/0125784 A1    May 10, 2018

Related U.S. Application Data

(63) Continuation of application No. 15/023,098, filed as application No. PCT/EP2014/070128 on Sep. 22, 2014, now Pat. No. 9,895,314.

(30) Foreign Application Priority Data

Sep. 20, 2013 (EP) .................................. 13185334

(51) Int. Cl.
| | |
|---|---|
| *A61K 9/16* | (2006.01) |
| *A61K 9/50* | (2006.01) |
| *A61K 31/192* | (2006.01) |
| *A61K 31/4164* | (2006.01) |
| *A61K 31/4178* | (2006.01) |
| *A61K 31/4422* | (2006.01) |

(52) U.S. Cl.
CPC .......... *A61K 9/1611* (2013.01); *A61K 9/1617* (2013.01); *A61K 9/50* (2013.01); *A61K 9/5005* (2013.01); *A61K 9/5026* (2013.01); *A61K 31/192* (2013.01); *A61K 31/4164* (2013.01); *A61K 31/4178* (2013.01); *A61K 31/4422* (2013.01)

(58) Field of Classification Search
CPC ...... A61K 9/16; A61K 9/5005; A61K 9/1611; A61K 9/50; A61K 9/1617
See application file for complete search history.

(56) References Cited

U.S. PATENT DOCUMENTS 9,895,314 B2 * 2/2018 Preisig ................. A61K 9/1617

FOREIGN PATENT DOCUMENTS

| CN | 101601862 | 7/2009 |
|---|---|---|
| EP | 2 168 572 A1 | 2/2010 |
| WO | WO 1999/027912 A1 | 6/1999 |
| WO | WO 1999/065463 A1 | 12/1999 |
| WO | WO 2003/080029 A1 | 10/2003 |
| WO | WO 2008/023999 A1 | 2/2008 |
| WO | WO 2010/037753 A1 | 4/2010 |

* cited by examiner

*Primary Examiner* — Carlos A Azpuru
(74) *Attorney, Agent, or Firm* — Chalin A. Smith; Smith Patent, LLC

(57) ABSTRACT

The present invention relates to a delayed release pharmaceutical formulation for delivering an active agent to the intestine, a method of preparing such formulation and the use of such formulation in the treatment of gastrointestinal disorders.

13 Claims, 7 Drawing Sheets

✦ Active agent
● Porous carrier particle
○ Mucoadhesive coating
▬ Coating for intestinal targeting

DELAYED RELEASE PHARMACEUTICAL FORMULATION AND METHODS OF MAKING AND USING SAME

PRIORITY

This application is a continuation of U.S. application Ser. No. 15/023,098 filed Mar. 18, 2016, which, in turn, corresponds to the U.S. national phase of International Application No. PCT/EP2014/070128, filed Sep. 22, 2014, which, in turn, claims priority to European Patent Application No. 13.185334.3, filed Sep. 20, 2013. The contents of these priority applications are incorporated by reference herein in their entirety.

FIELD OF THE INVENTION

The present invention relates to a delayed release pharmaceutical formulation for delivering an active agent to the intestine, a method of preparing such formulation and the use of such formulation in the treatment of gastrointestinal disorders.

BACKGROUND OF THE INVENTION

The local treatment of bowel diseases, such as Crohn's disease and ulcerative colitis, or the targeting of drugs to the intestine and in particular to the colon for systemic administration is highly challenging because conventional dosage forms rapidly release the drug in the upper gastrointestinal tract. Upon absorption into the blood stream, the drug is distributed throughout the human body, resulting in potentially severe side effects. In addition, the drug concentration at the site of action, such as the inflamed colon, is low, leading to low therapeutic efficacies. To overcome these restrictions, drug release from the dosage form should ideally be suppressed in the stomach and small intestine, but set on as soon as the target site is reached.

Different approaches have been described in the prior art to allow for site-specific drugs delivery to the small and/or large intestine upon oral administration. Generally, a drug reservoir is surrounded by a film coating, which is poorly permeable to the drug in the upper gastrointestinal tract, but becomes permeable as soon as the target site is reached. Furthermore, drug release might start right after oral administration at a rate which is sufficiently small in order to assure that drug is still present in the dosage form once the target site is reached.

Release of drugs in the colon typically requires a different approach than the release in the small intestine. The colon is susceptible to a number of disease states, including inflammatory diseases, irritable bowel syndrome, constipation, diarrhea, infection and carcinoma. In such conditions, drug targeting to the colon would maximize the therapeutic effectiveness of the treatment. The colon can also be utilized as a portal for the entry of drugs into the systemic circulation and therefore can be effective in the treatment of diseases outside the colon.

Various formulations have been developed for intestinal and in particular colonic drug delivery, including pro-drugs as well as formulated dosage forms, with the latter being more popular since the concept once proofed can be applied to other active agents. Examples for devices and dosage forms for controlled release of an active agent to the colon can be found in U.S. Pat. No. 4,627,851, WO 83/00435 and WO 2007/122374.

Another problem is that colonic diseases are often associated with an insufficient water-resorption and thus a significantly reduced residence time of the drug at the site of action. In order to prevent immediate wash-out a fast release of the drug from the formulation immediately after entering the colon is required. On the other hand, a fast release of the drug is associated with the risk of dose dumping in the upper gastrointestinal tract, for example if the delayed release coating is damaged or for some other reason not sufficient for preventing premature drug release.

Furthermore, the site-specific release of an active agent to the intestine and in particular the colon is extremely sensitive to inter-individual variability. The release is dependent on the individual environment in the gastrointestinal tract, like pH or bacterial flora. This is even true for different stages of inflammation of the mucosa in the small intestine due to individual pH shifts compared to non-inflamed mucosa. This problem occurs for example in ulcerative colitis at different stages of inflammation or in Crohn's disease with different sections of the small intestine affected. This makes it difficult to tailor drug delivery in a way that the drug release takes place not earlier than for example in the terminal ileum.

Even though a variety of technical means to accomplish controlled release and especially site-specific release to the colon is known, there is an incessant need for further pharmaceutical formulations which tailor the delivery of drugs and adapt it to new requirements. Especially for the treatment of inflammations of the mucosa of the small intestine and in particular the colon further pharmaceutical formulations are required which reliably prevent an early release of the drug but at the same time provide release of the drug during its stay at the site of action. Additionally, any excipients in such formulations should be low or not irritating in order to keep the mucosa protected from further irritation.

SUMMARY OF THE INVENTION

Thus, the present invention relates to the problem of providing further means for tailoring drug delivery to the intestine and in particular to the colon. At the same time, the formulation should have low irritating effect on the mucosa. The release of the drug should start immediately when the formulation has reached the intestine and preferably the terminal ileum so that the full dose of the formulation can be released during the passage through the intestine and preferably the colon.

Precipitated calcium carbonate has been widely used as additives in the paper and food industry and intensely evaluated as possible pharmaceutical excipient. In 2000, a novel, highly porous structure of calcium carbonate, called functionalized calcium carbonate or modified calcium carbonate, was described as a pigment filler or a mineral (WO 00/39222). An improved process for preparing such functionalized (surface-reacted) calcium carbonate and the use of such functionalized calcium carbonate in paper, tissue paper, plastics, paints, or as a controlled release or water treatment agent is disclosed in EP-A-2 264 108.

T. Stirnimann et al. describe in Pharm Res, published online on Apr. 19, 2013 the use of functionalized calcium carbonate as a pharmaceutical excipient for the preparation of orally dispersible tablets.

In WO 2010/037753 a carrier for the controlled release of active agents, comprising functionalized (surface-reacted) calcium carbonate is disclosed. In the examples, natural oils such as amaranth, peppermint oil and limonene are used as active agents and the tablets prepared from the carrier containing the active agent are used as bath bombs, bath tablets, toothpastes and skin care formulations.

It has now surprisingly been found that porous particles, such as functionalized calcium carbonate, have excellent properties in pharmaceutical formulations for delivering an active agent to the intestine. Porous particles have the ability to adsorb and absorb a high amount of active agent resulting in a high drug load. Furthermore, it was found that the drug is very quickly released from porous particles. Additionally, due to the small size of porous particles a high number of small individual particles are released from a pharmaceutical formulation containing these particles which can then spread over a large area of the intestine for releasing the active agent.

The present invention therefore relates to a delayed release pharmaceutical formulation for delivering an active agent to the intestine, comprising carrier particles and at least one active agent associated with the carrier particles, wherein the carrier particles are porous and are surrounded by a material for intestinal targeting.

DETAILED DESCRIPTION OF THE PREFERRED EMBODIMENTS

Figure 1:
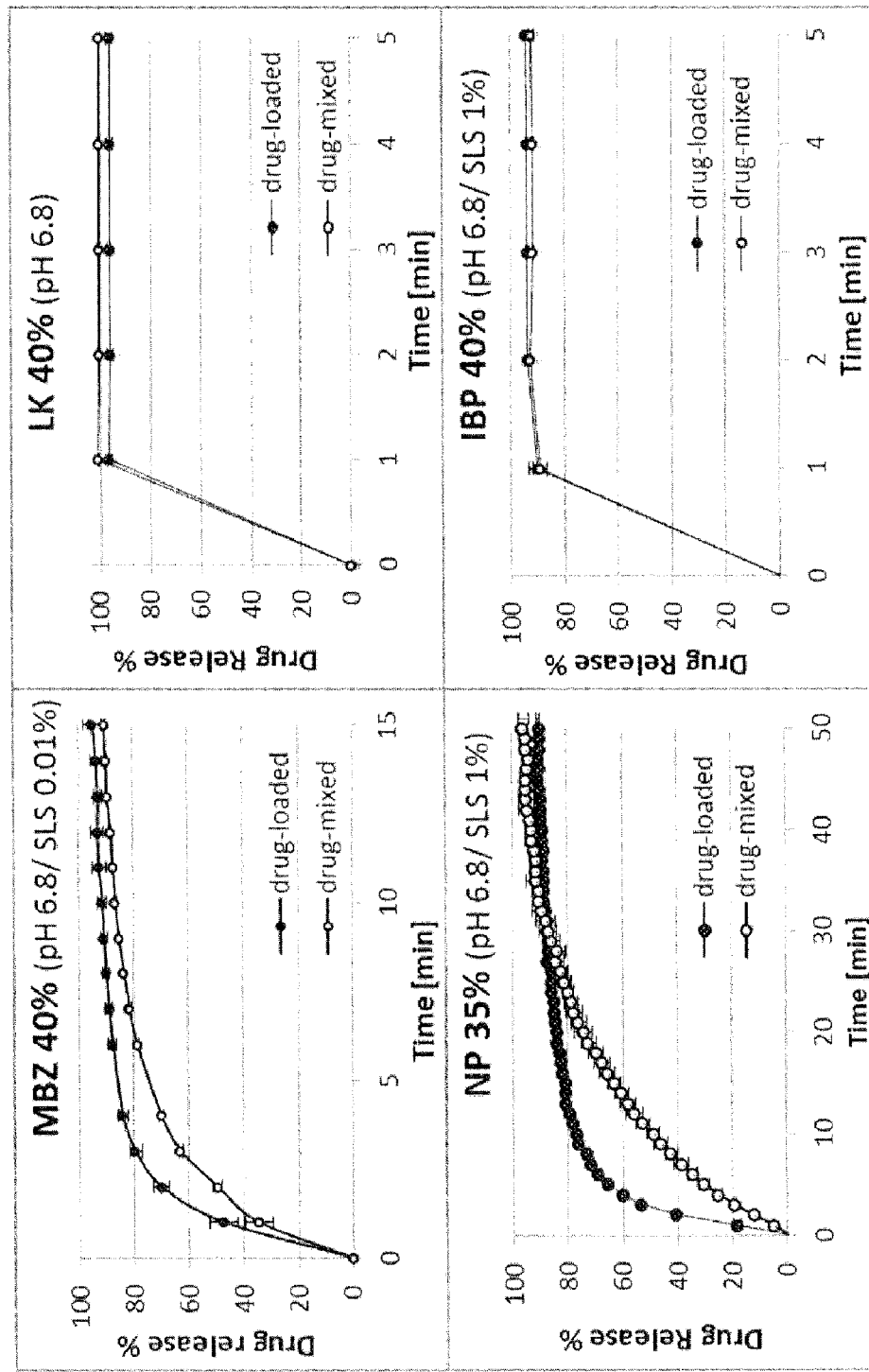
FIG. 1 shows dissolution profiles from FCC loaded with metronidazole benzoate (MBZ), ibuprofen (IBU), losartan potassium (LK) and nifedipine (NP) in comparison to physical mixtures of drug and FCC with same drug content.

A delayed release pharmaceutical formulation is understood as being a formulation which delays the release of the active agent from the time of oral administration until the formulation reaches at least the intestine, preferably the terminal ileum, so that the active agent is substantially released in the intestine and preferably the colon only. Once the formulation has reached at least the intestine and release of the active agent starts, the release may be immediate or slowly over time.

As carrier particles any porous particles being pharmaceutically acceptable may be used. The carrier particles are preferably selected such that they do not react with the active agent. For example, silicon dioxide, magnesium aluminometasilicate, aluminosilicate, calcium silicate, calcium carbonate, calcium phosphate, titanium dioxide, zirconium dioxide and other ceramics may be used as carrier particles.

The size of the carrier particles is not particularly limited and may be selected by the skilled person according to the requirements. For example, the carrier particles without active agent or any coating material can have a weight median grain diameter $d_{50}$ of from less than 1 mm, more preferably of less than 0.1 mm and most preferably of less than 0.05 mm, such as from 0.1 to 50 μm, more preferably from 0.5 to 25 μm, even more preferably from 0.8 to 20 μm, such as from 1 to 10 μm, measured according to the sedimentation method. Thus, the carrier particles can for example be micro and nano particles.

The porosity of the carrier particles is related to their specific surface area which preferably is in the range of from 5 $m^2/g$ to 200 $m^2/g$, more preferably from 20 $m^2/g$ to 80 $m^2/g$ and most preferably from 30 $m^2/g$ to 60 $m^2/g$, measured using nitrogen and the BET method according to ISO 9277.

In a preferred embodiment the carrier particles comprise calcium carbonate, in particular precipitated or functionalized calcium carbonate. Preferably, the carrier particles consist of functionalized calcium carbonate. The advantage of functionalized calcium carbonate particles over other particles is that they are non-toxic and that they degrade or dissolve fast, in particular at lower pH. Thus, they have no or only little irritating effect on the mucosa of the intestine, in particular of the colon.

Functionalized calcium carbonate is known in the art. It is a highly porous variation of precipitated calcium carbonate. As a result of its small pore size and enlarged surface area it is called "functionalized calcium carbonate" (FCC). Four different types of FCC (S01, S01, S03 and S04) with different particle size, pore size and pore structure are currently commercially available from Omya.

FCC can be prepared as described in WO 00/39222 and EP-A-2 264 108. Since it is prepared by reaction of the surface of natural or synthetic calcium carbonate with carbon dioxide and an acid, FCC is also called "surface-reacted calcium carbonate". Thus, FCC is obtainable by reacting natural or synthetic calcium carbonate with carbon dioxide and one or more acids, wherein the carbon dioxide is formed in situ by the acid treatment and/or is supplied from an external source as described for example in WO 2010/037753.

The natural calcium carbonate from which the FCC is prepared can be selected for example from the group comprising marble, calcite, chalc and dolomite, limestone and mixtures thereof. The synthetic calcium carbonate from which the FCC may be prepared preferably is precipitated calcium carbonate including aragonitic, vateritic or calcitic mineralogical crystal forms or mixtures thereof. The acids used in the preparation of FCC can be selected from hydrochloric acid, sulfuric acid, sulfurous acid, hydrosulphate, phosphoric acid, oxalic acid and mixtures thereof.

The FCC preferably has a specific surface area of from 5 $m^2/g$ to 200 $m^2/g$, more preferably from 20 $m^2/g$ to 80 $m^2/g$ and most preferably from 30 $m^2/g$ to 60 $m^2/g$, measured using nitrogen and the BET method according to ISO9277.

The FCC preferably has a weight median grain diameter $d_{50}$ of from 0.1 to 50 μm, more preferably from 0.5 to 25 μm, even more preferably from 0.8 to 20 μm, particularly from 1 to 10 μm measured according to the sedimentation method.

The FCC preferably has an intra-particle porosity determined as the pore volume per unit particle volume within the range of from 20 vol.-% to 99 vol.-%, more preferably from 30 vol.-% to 70 vol.-%, even more preferable from 40 vol.-% to 60 vol.-%, such as about 50 vol.-%, calculated from a mercury porosimetry measurement.

The carrier particles, such as FCC, are capable of associating active agents. The association can be an adsorption onto the surface of the particles, be it the outer or the inner surface of the particles or an absorption into the particles. Adsorption and absorption of the active agent is essentially controlled by the pore size, which preferably is in the range of from 10 to 100 nm, more preferably in the range of between 20 and 80 nm, especially from 30 to 70 nm, such as about 50 nm.

Loading of the particles with the active agent can be conducted by any suitable method known to a person skilled in the art, such as by soaking the particles with a solution of the active agent in a suitable solvent, separating the soaked particles from the solution, for example by filtration or centrifugation and drying the so obtained soaked particles. However, it was found that loading the particles by this method results in low drug loads of only up to about 10% by weight based on the total weight of the carrier particles including the weight of the active agent. This has the disadvantage that high amounts (and volumes) of the final formulation must be administered in order to provide sufficient active agent to a patient.

It has surprisingly been found that the drug load can considerably be increased if the active agent is adsorbed/absorbed by the particles using an evaporation method. In this method, the unloaded particles are dispersed in a solution of the active agent in a suitable solvent wherein the solution contains the desired total amount of active agent to be loaded onto and into the particles. The suspension is then evaporated thereby allowing the active agent to deposit on and in the particles. Using this method yields carrier particles being associated with at least 15% by weight, preferably at least 20% by weight, more preferably at least 30% by weight, even more preferably at least 40% by weight, such as about 45% by weight of the at least one active agent based on the total weight of the carrier particles including the weight of the at least one active agent.

Adsorption/absorption of the active agent on/in the porous particles by evaporation can be conducted using usual evaporation methods, such as by letting the solvent evaporate in an open vessel, for example at room temperature or increased temperature, at room pressure or in a closed vessel at decrease pressure. These methods, are, however, time consuming and on an industrial scale it can therefore be of advantage to adsorb/absorb the active agent on/in the porous particles using a fluid-bed coating technique also known to the skilled person. Alternatively, the active agent may be adsorbed/absorbed by known spray drying methods, for example by spray drying a solution of the active agent together with suspended porous particles.

The active agent which may be used in association with the particles is not particularly limited and can be selected by the skilled person according to the needs. For example, the active agent can be selected from the group consisting of anti-inflammatory agents, anti-infective agents, immunomodulators and antibodies. The anti-inflammatory agent can for example be a steroid, a corticosteroid, a non-steroidal anti-inflammatory agent or a herbal anti-inflammatory agent. The anti-infective agent can for example be an antibiotic, a virustatic, an antimycotic, an anthelmintic or an agent against other micro-organisms (e.g. algae). Specific examples of suitable active agents are 5-aminosalicylic acid, prednisolone, budesonide, fluticasone, azathioprine, cyclosporine, metronidazole and methotrexate. The active agent can be present in its free base or acid form or as any pharmacologically acceptable derivative, such as ester, and/or salt thereof.

In the formulation of the present invention the carrier particles are surrounded by a material for intestinal, preferably colon targeting. It is understood that "surrounded" means that the carrier particles are surrounded by the material for intestinal targeting such that the material substantially prevents and preferably completely prevents release of the active agent before the formulation reaches the intestine, preferably before it reaches the terminal ileum, most preferably before it enters the colon. This goal can be achieved by surrounding the carrier particles by a coating of the material for intestinal targeting. The coating can be applied to each individual carrier particle or to a core comprising a plurality of carrier particles, such as a tablet core. In a further embodiment the coating can be applied to a capsule, such as a hard gelatin capsule, containing the carrier particles. It is also envisaged that the carrier particles can be combined into larger particles, such as granules, pellets or minitablets. These individual larger particles may then be coated with the material for intestinal targeting and filled for example into sachets or capsules. Thus, "surrounded" does not mean that the carrier particles are necessarily directly surrounded by the material for intestinal targeting but the material may be present in a shell or coating being not in direct contact with the carrier particle.

In an alternative embodiment the carrier particles are within a matrix of the material for intestinal, preferably colon targeting. Non-coated multiparticlulate matrix systems for colon targeting are for example described by S. Krenzlin in Drug Development and Industrial Pharmacy, 2011, 37(10):1150-1159.

The pharmaceutical formulation comprising the carrier particles being surrounded by a coating of the material of intestinal targeting may comprise one or more further coatings being above or below for example the coating of the material for intestinal targeting or being between the carrier particles and the matrix of the material for intestinal targeting. It is also possible that the carrier particles are first embedded within a matrix of the material for intestinal targeting and the thus obtained larger particles are then coated with a further coating of the same or a different material for intestinal targeting.

Materials for intestinal targeting which can be used for surrounding the carrier particles in the formulation of the present invention are well known to a person skilled in the art. Preferably, the material comprises a compound which is insoluble in the gastrointestinal juice at a pH of below 5 and which is soluble in the intestinal juice at a pH at or above 5. Thus, this material dissolves in a pH dependent manner. The material has a pH threshold which is the pH below which it is insoluble and at or above which it is soluble. The pH of the surrounding medium triggers the solution of the material. Thus, none (or essentially none) of the material dissolves below the pH threshold. Once the pH of the surrounding medium reaches (or exceeds) the pH threshold, the material becomes soluble.

By "insoluble" it is understood that 1 g of the material requires more than 10,000 ml of solvent (surrounding medium) to dissolve at a given pH. By "soluble", it is understood that 1 g of the material requires less than 10,000 ml, preferably less than 5,000 ml, more preferably less than 1,000 ml, even more preferably less than 100 ml or 10 ml of solvent to dissolve at a given pH. "Surrounding medium" means the medium in the gastrointestinal tract, such as the gastric juice or intestinal juice. Alternatively, the surrounding medium may be an in vitro equivalent of the medium in the gastrointestinal tract.

The normal pH of gastric juice is usually in the range of 1 to 3. The material for intestinal, preferably colon targeting is insoluble below pH 5 and soluble at or above pH 5. The material therefore is usually insoluble in gastric juice. Such material may be referred to as an "enteric" material. The pH of intestinal juice gradually increases to about 7 to 8 along the small intestine. The material for intestinal targeting therefore becomes soluble in the terminal ileum/colon and allows release of the active agent from the carrier particles. The material preferably has a pH threshold of 6.5, more preferably of 7.

Examples of suitable materials for intestinal targeting and in particular for the preparation of a coating surrounding the carrier particles are acrylate polymers, cellulose polymers and polyvinyl-based polymers, chitosan, its derivatives or other polymers. Examples of suitable cellulose polymers include cellulose acetate phthalate, cellulose acetate trimellitate and hydroxypropylmethyl cellulose acetate succinate. Examples of suitable polyvinyl-based polymers include polyvinylacetate phthalate.

In one embodiment the material for intestinal targeting can be a co-polymer of a (meth)acrylic acid and a (meth)acrylic acid $C_{1-4}$ alkyl ester, for instance, a copolymer of methacrylic acid and methacrylic acid methyl ester. Suitable examples of such copolymers are usually anionic and not sustained release polymethacrylates. The ratio of carboxylic acid groups to methylester groups in these co-polymers determines the pH at which the copolymer is soluble. The acid:ester ratio may be from about 2:1 to about 1:3, e.g. about 1:1 or, about 1:2. The molecular weight of such anionic copolymers is usually from about 120,000 to 150,000, preferably about 135,000.

Known anionic poly(methycrylic acid/methyl methacrylate) co-polymers include Eudragit® L (pH threshold about 6.0), Eudragit® S (pH threshold about 7) and Eudragit® FS (pH threshold about 7). Eudragit® L 100-55 which is a copolymer of methacrylic acid and ethylacetate and which has a pH threshold of about 5.5 is also suitable. The Eudragit® copolymers can be obtained from Evonik.

Mixtures of two or more materials for intestinal targeting may be used as appropriate.

Optionally, conventional excipients such as plasticizers for film formation (for example triethylcitrate) and anti-tacking agents (such as glyceryl monostearate) may be included in amounts up to 30% by weight of the total weight of the coating preparation.

The thickness of the coating surrounding the carrier particles is typically from about 10 μm to about 150 μm. The thickness of a specific coating will, however, depend on the composition of the coating and surface area of the carrier.

In addition or alternatively to the above described compounds having a pH threshold the material for intestinal, preferably colon targeting may comprise a compound which is susceptible to attack by colonic bacteria, such as polysaccharides. Suitable polysaccharides are for example starch, amylose, amylopectine, chitosan, chondroitine sulfate, cyclodextrine, dextrane, pullulan, carrageenan, scleroglucan, chitin, curdulan and levan.

Furthermore, Nutriose® is suitable as material for colon targeting, in particular for forming a matrix surrounding the carrier particles. Nutriose® is a water-soluble, branched dextrin with high fiber contents obtained from wheat starch which is commercially available from Roquette Freres. This compound may be used in combination with for example microcrystalline cellulose, polyvinylpyrolidone or lipids, such as hardened soy bean oil, glyceryl tristearate, sasol wax, microwax HG, microwax HW, or the like.

The pharmaceutical formulation of the present invention may contain further pharmacologically acceptable excipients known to a person skilled in the art. For example, the carrier particles can be directly compressed into tablet cores either alone or in combination with usual fillers, lubricants, etc. and the tablet core can then be surrounded by the material for intestinal targeting. In another embodiment the carrier particles can be granulated into granules either alone or in combination with usual excipients, such as fillers or granulation aids before they are either compressed into tablet cores or directly surrounded by the material for intestinal targeting.

The final pharmaceutical formulation is an oral dosage form intended for oral administration and being in the form of for example tablets, granules, mini-tablets, pellets or capsules.

The pharmaceutical formulation of the present invention has the advantage that the carrier particles generally have a small particle size. Therefore, the pharmaceutical formulation contains a high number of individual carrier particles which may separate from each other when the formulation disintegrates upon dissolution of the material for intestine targeting. Thus, a high number of carrier particles are released and can spread over a large area of the intestine thereby resulting in a uniform release of the active agent within the intestine.

Furthermore, the release of the active agent from the carrier particles depends on the size of the carrier particles and the size of their pores as well as of the physical and chemical properties of the active agent itself. Thus, in some cases, the active agent is immediately released from the carrier particles while in other cases the active agent may be released over a prolonged time period. It would therefore be desirable to provide means for tailoring the release profile of a given active agent according to the specific needs of the patient or the disease to be treated.

Furthermore, it was found that for example lipophilic active agents tend to be difficult to be loaded onto and into the carrier particles. It would therefore be desirable to provide carrier particles allowing a higher drug load in particular for lipophilic active agents.

It was surprisingly found that both problems can be solved by coating the carrier particles at least partially with a compound which imparts hydrophobicity or hydrophilicity to the surface of the carrier particles. This can be accomplished for example by reacting the carrier particles and in particular the functionalized calcium carbonate with a hydrophobic or hydrophilic compound, such as a fatty acid, for example a stearic acid. It has been found that such compounds react with the surface of the functionalized calcium carbonate thereby forming a film or coating of for example stearate molecules. These molecules impart for example hydrophobicity to the surface of the carrier particles and thereby allow for a higher load of a hydrophobic drug. Furthermore, if for example a hydrophobic drug is loaded onto and into a hydrophobically modified carrier particles, the release of the active agent is retarded and the active agent will be available in the intestine over a prolonged time period.

In a further embodiment the carrier particles in the pharmaceutical formulation of the present invention are at least partially coated with a mucoadhesive compound.

Coating the particles with a mucoadhesive compound has the advantage that the carrier particles are retained in the intestine for a prolonged time so that the active agent may be released also for a prolonged time without the risk that the carrier particles leave the intestine before the active agent has been sufficiently released. The retention of the particles at the mucosal surface can contribute to extended residence time in the target region.

Suitable mucoadhesive compounds are known to a person skilled in the art. Examples for synthetic mucoadhesive polymers are the various acrylic acid derivatives, in particular polyacrylates (also known as carbomers which are commercially available as Carbopols®), polyvinylpyrrolidone (PVP), and polyvinylalcohol. Alginate, pectin and guar gum can be mentioned for natural mucoadhesive polymers. Chitosan and many cellulose derivatives are known as semi-synthetic mucoadhesive polymers.

Figure 7:
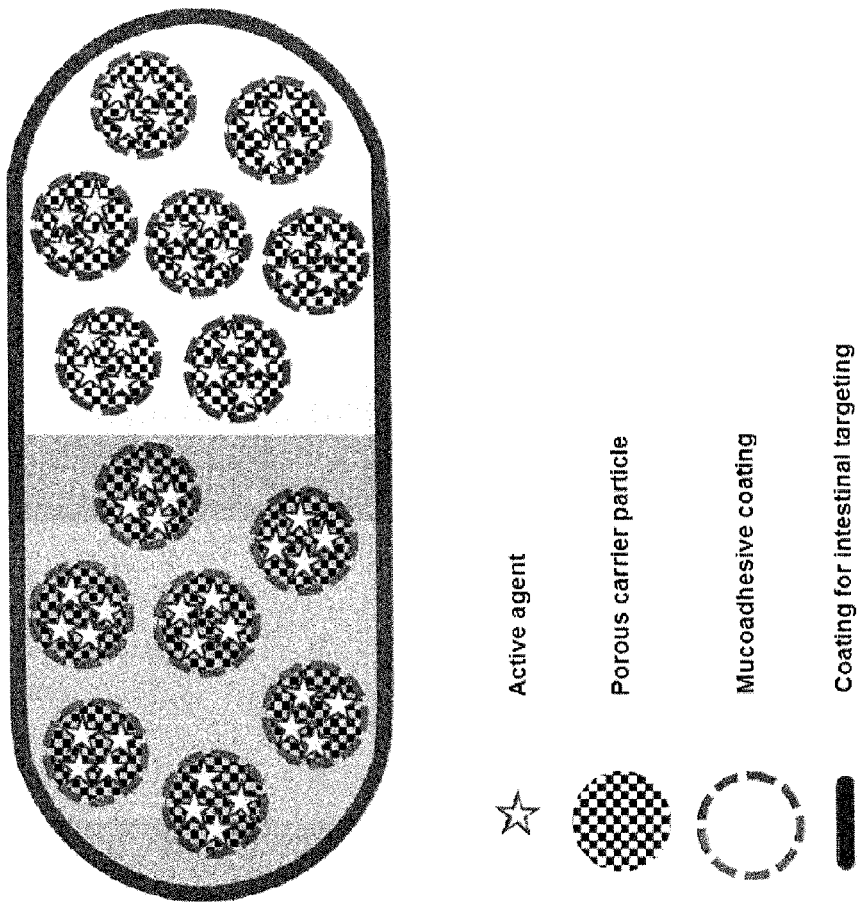
FIG. 7 schematically shows one example of a pharmaceutical formulation according to the invention.

An example for a pharmaceutical formulation according to the invention is schematically shown in FIG. 7. This figure shows active agent associated with carrier particles which are coated with a mucoadhesive compound. The such coated particles are contained within a capsule which is surrounded by a coating for intestinal targeting.

In a further embodiment the carrier particles in the pharmaceutical formulation of the present invention are at least partially coated with a sustained release coating. The sustained release coating may be present instead of the mucoadhesive compound or in combination with the mucoadhesive compound. Preferably, the carrier particles are at least partially coated with both, a mucoadhesive compound and a sustained release coating because in this case, the carrier particles are retained in the intestine for a prolonged time and simultaneously the active agent is released over a prolonged time.

Suitable compounds for preparing the sustained release coating are known to the skilled person. For example, Eudragit RS, Eudragit RL, Eudragit NM, Eudragit NE, ethyl cellulose, Compritol ATO 888, Precirol ATO 5, Geleol Mono and Diglycerides NF may be used.

The sustained release coating may be applied onto the porous particles simultaneously with the mucoadhesive compound or before or after the mucoadhesive compound. Preferably, the particles are first at least partially coated with the sustained release coating and afterwards the mucoadhesive compound is applied to the such coated particles.

The present invention furthermore provides a method of preparing the above described delayed release pharmaceutical formulation. This method comprises the steps of loading porous carrier particles, such as functionalized calcium carbonate, with at least one active agent to obtain loaded carrier particles and surrounding the loaded carrier particles with a material for intestinal, preferably colon targeting.

Loading the carrier particles with the active agent can be conducted by conventional methods as described above. In one embodiment loading is conducted by suspending the carrier particles in a solution of the active agent in a suitable solvent, such as an alcohol, in particular ethanol or methanol, any other organic solvent, such as acetone, or water. The solvent is then removed from the suspension by evaporation, preferably under reduced pressure. Alternatively, the carrier particles can be loaded with the active agent by a fluid-bed coating technique or by spray drying.

Surrounding the loaded carrier particles with the material for intestinal targeting can be conducted by usual methods, such as spray coating for obtaining a coating, or extrusion methods, such as melt extrusion, for obtaining a matrix.

The method may comprise other steps such as granulation and/or compression steps of the loaded carrier particles alone or in combination with one or more excipients.

Furthermore, the present invention relates to the above described delayed release pharmaceutical formulation for use in a method of treatment of gastrointestinal disorders, such as inflammatory disorders of the gastrointestinal tract including Crohn's disease and ulcerative colitis, inflammatory bowel disease, constipation, diarrhea, infection, and carcinoma, particularly colon or colorectal cancer.

The invention will now be further explained by the following examples which are not intended to be construed as limiting.

EXAMPLE 1

Drug-loaded FCC (dl-FCC) was produced with metronidazole benzoate (MBZ), ibuprofen (IBU), losartan potassium (LK) and nifedipine (NP) in different drug to drug-carrier ratios. The series of different drug loads (DL) included 25, 30, 35, 40, 45 and 50% (w/w).

The weighted drug was put in a round bottom flask and dissolved in 50 ml of the organic solvent. Acetone served as drug loading solvent for IBU, MBZ and NP, whereas LK was dissolved in methanol. Bulk FCC (5.0 g) was added and sonicated (Retsch, Switzerland) for 5 min to disperse the particles and degas the solvent. The solvent was evaporated in a rotary evaporator (Büchi RE 121 or R-114) with a waterbath set to 40° C. (Büchi 461 or B-480). Pressure was stepwise decreased by 100 mbar per 0.5 h down to 20 mbar, and held for at least 1 hour. Initial pressure setting was 300 mbar for methanol and 480 mbar for acetone. After removal of the residual solid from the round bottom flask, the product was gently milled with mortar and pestle, and subsequently sieved through 250 µm and 90 µm mesh screens (Retsch, Switzerland). The dl-FCC was vacuum dried for 24 h at room temperature (KVTS 11, Salvis AG, Switzerland) under constant nitrogen injection.

Drug release of IBU, LK, MBZ and NP was studied with a USP2 dissolution apparatus (SOTAX, Switzerland). Dissolution buffer (pH 6.8, 0.05 M) consisting of sodium phosphate was produced according to the standards of the international Pharmacopoeia. Addition of sodium lauryl sulphate (SLS) was necessary to reduce surface tension of the medium and to assure sinking of the drug-loaded and drug-mixed formulations. The dissolution medium was continuously transferred to the UV-spectrophotometer (Amersham Bioscience, Ultrospec 3100 pro) and returned back to the dissolution vessels with a peristaltic pump (IPC, Ismatec, Switzerland). Absorbance was measured every minute at the wavelengths described in the HPLC-UV methods. Samples were measured in duplicates (NP) or triplicates and sink conditions were provided in all experiments. Path length of the cells was adjusted (0.2 or 1.0 cm) to obtain absorbances in the linear and valid range of the calibration standard.

FIG. 1 shows dissolution plots of drug-loaded FCC in comparison to physical mixtures of drug and FCC (dm-FCC). Immediate and complete drug release within the first minute was observed for LK- and IBU-loaded FCC and corresponding reference formulations (dm-FCC). In contrast, MBZ- and NP-loaded FCC showed faster drug dissolution in comparison to the drug-mixed FCC. After 3 min, 80% was released from MBZ-loaded FCC, whereas 6 min passed until 80% of the MBZ-mixed formulation were dissolved. NP-loaded FCC was releasing the first 80% 2.5-fold faster than the NP-mixed FCC. In summary, the investigated drug-loaded FCC formulations provided immediate drug release and showed no reduction in dissolution rate, but faster release for NP- and MBZ-loaded FCC.

EXAMPLE 2

2.1 Drug Loading

Drug loading was performed with 5 or 5.5 g of FCC S01 and varying amounts of MBZ. Acetone was used to dissolve MBZ and disperse FCC. The solvent was removed and MBZ re-crystallized on the surface of FCC. The solvent evaporation method allowed controlling the resulting mass fraction of the drug. Drug-load levels of 20%, 30%, 35%, 40%, 45% and 50% (w/w) were produced.

The weighted MBZ was put in a round bottom flask and dissolved in 50 ml acetone. The required amount of FCC was added and sonicated for 5 min to disperse the FCC and degas the solvent. Acetone was evaporated at 40° C. and 480 mbar using a rotary evaporator (Büchi RE 121 or R-114) and a water bath (Büchi 461 or B-480). The pressure was stepwise decreased to 400, 300, 100, and 5 mbar in intervals of 0.5 h. The average speed of pressure drop was approximately 200 mbar/h. The residual solid was removed from the round bottom flask, transferred into a petri dish and vacuum dried overnight at room temperature.

2.2 SEM Characterization

Figure 2A:
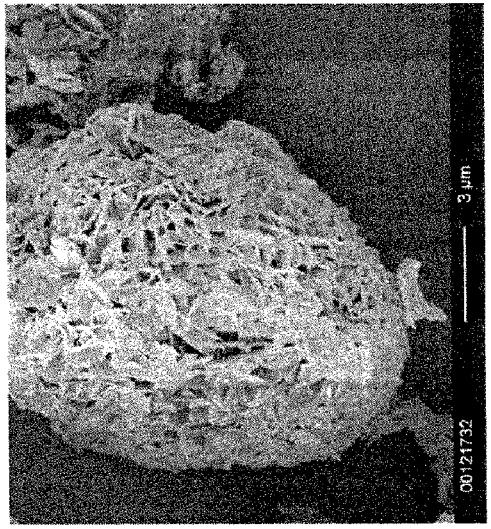
FIG. 2A shows an SEM picture of an unloaded FCC particle.

A differentiated characterization of FCC particles by Scanning Electron Microscopy (SEM) was conducted to evaluate the morphological difference after the drug-loading procedure. An unloaded FCC particle is shown in FIG. 2A. The outer surface of FCC is built up by interconnected panels, which is a main morphological characteristic of FCC. FIG. 2A shows a typical picture of the distinctive pore structure.

Figure 2B:
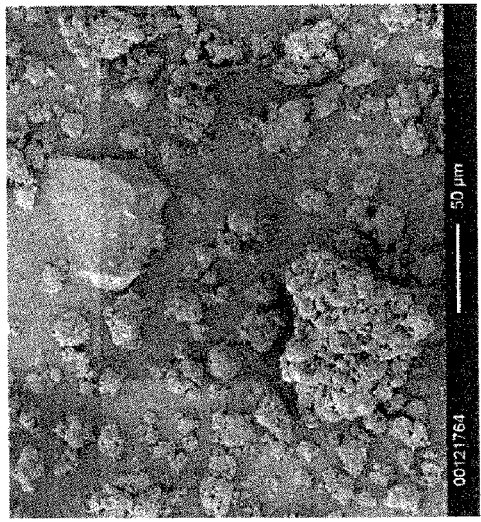
FIG. 2B shows an SEM picture of an FCC particle with a MBZ drug load of 20%.

SEM analysis of FCC particles with a MBZ drug load of 20% showed individual particles without agglomerates. FCC particles with notable pore filling were sparsely found. Most of the investigated particles showed no visible difference compared to unloaded FCC. A typical example is shown in FIG. 2B, where pore size and pore structure remained unchanged. These observations let assume that more drug could be loaded.

Figure 2C:
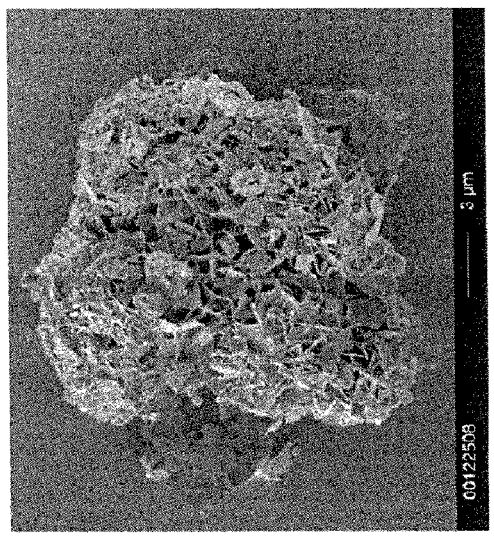
FIG. 2C shows an SEM picture of an FCC particle with a MBZ drug load of 40%.

Two batches of 40% DL were investigated and showed good reproducibility. No MBZ crystals (>2 µm) were observed and both batches revealed the same prevalence and size-range of agglomerates. All particles showed only a few free pores what indicated a reaching of the capacity limits for drug loading. FIG. 2C is a typical example of single FCC particles with a complete drug load. The upper edges of the characteristic FCC panels were stretching out of the surface, indicating that the pores were filled with the drug; and not just covered. Compared to unloaded FCC particles the surfaces were considerably smoother, but still exhibited a rough morphology.

Figure 2D:
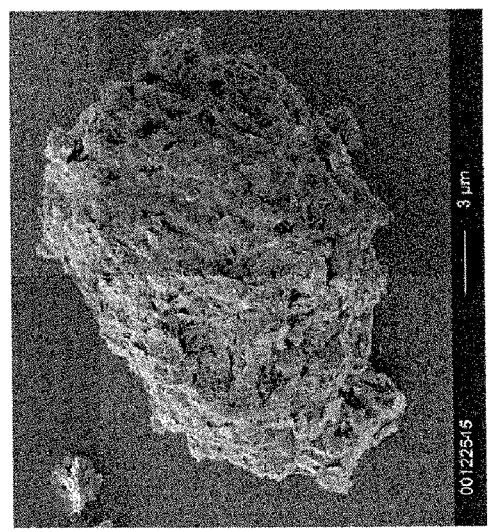
FIG. 2D shows an SEM picture of FCC particles with a MBZ drug load of 50%.

A drug load of 50% resulted in the formation of many agglomerates and big separate MBZ crystals (FIG. 2D). This observation demonstrated the limit of drug-load capacity of FCC in this particular example at 40-45%.

2.3 Dissolution

A mixture of 96% drug-loaded FCC (MBZ DL 40%) and 4% Ac-Di-Sol was produced and tablets of 500 mg (round shape, d=8 mm) were compacted with 10 kN (Styl'One, Medelpharm). Drug release of MBZ out of FCC was studied with a USP2 dissolution apparatus (SOTAX). The tablets were cut in half to achieve sink conditions in 1 l of de-ionized water. Average mass of MBZ was 97.7 mg per halved tablet. Samples were taken from the dissolution vessels every minute by a custom-built auto-sampler and absorbance was measured spectrophotometrically at 320 nm (Amersham Bioscience, Ultrospec 3100 pro). The peristaltic pump (Ismatec IPC) and the UV-spectrophotometer were controlled by a computer software.

Figure 3:
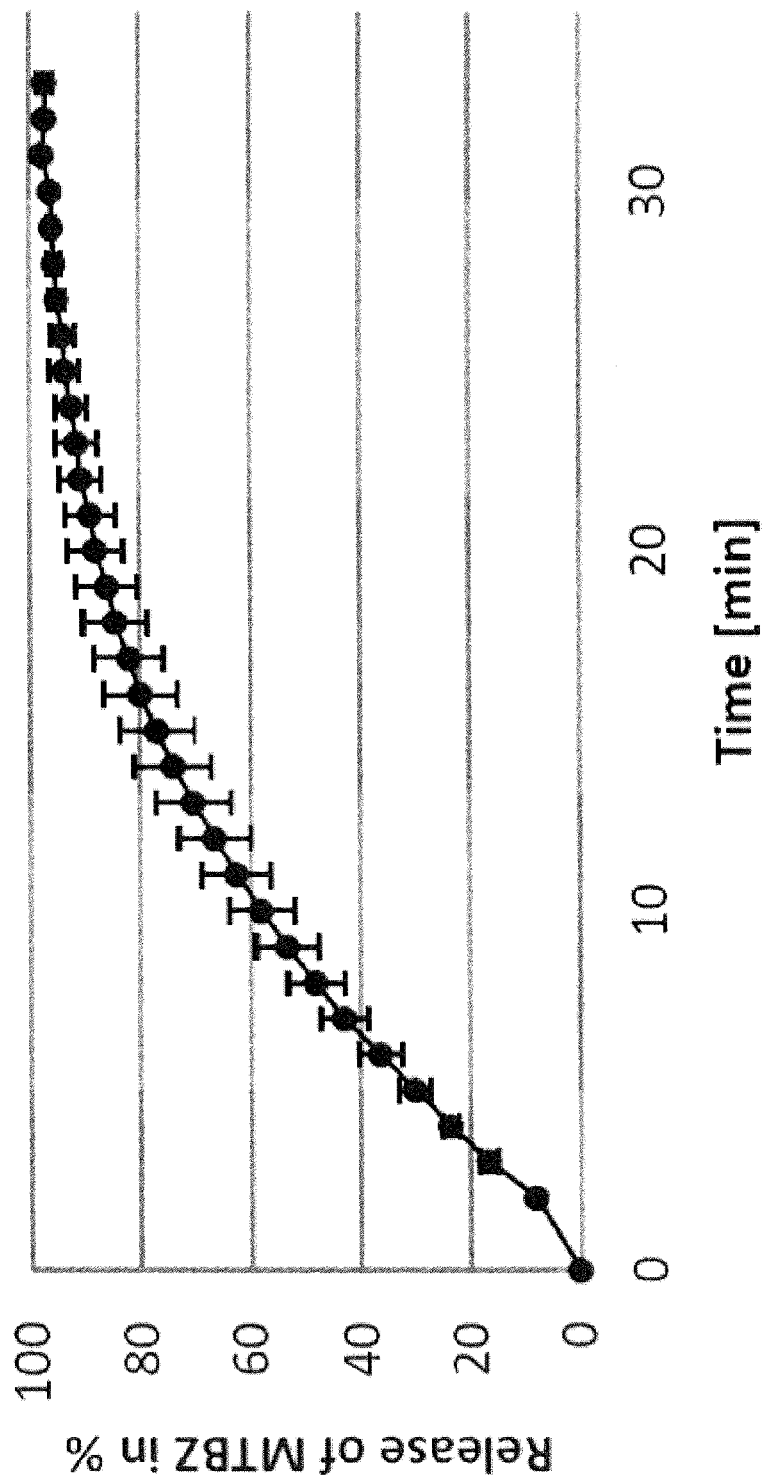
FIG. 3 shows the dissolution profile of the FCC formulation with 40% drug load of MBZ obtained in example 2.

Tablets were prepared to yield a hardness of 110 N. To measure the drug release from individual FCC particles, Ac-Di-Sol was used as superdisintegrant. The disintegration of the tablet into single particles happened within the first minute and the distribution of the drug-loaded sub-units simulated the desired performance in the colon. FIG. 3 shows the dissolution profile of the FCC formulation with 40% drug load of MBZ. A complete release of MBZ happened within 30 min.

2.4 Stability Testing

The compatibility of MBZ and FCC was investigated by an accelerated stability study. Drug loaded FCC particles with 20 and 50% drug content were stored at 25° C., 40° C. and 60° C. over a period of 25 days. On several days the MBZ content was analyzed by HPLC-UV.

Only the active substance (MBZ) was detected but not any degradation products from hydrolysis such as metronidazole (MTZ) or benzoic acid.

Figure 4:
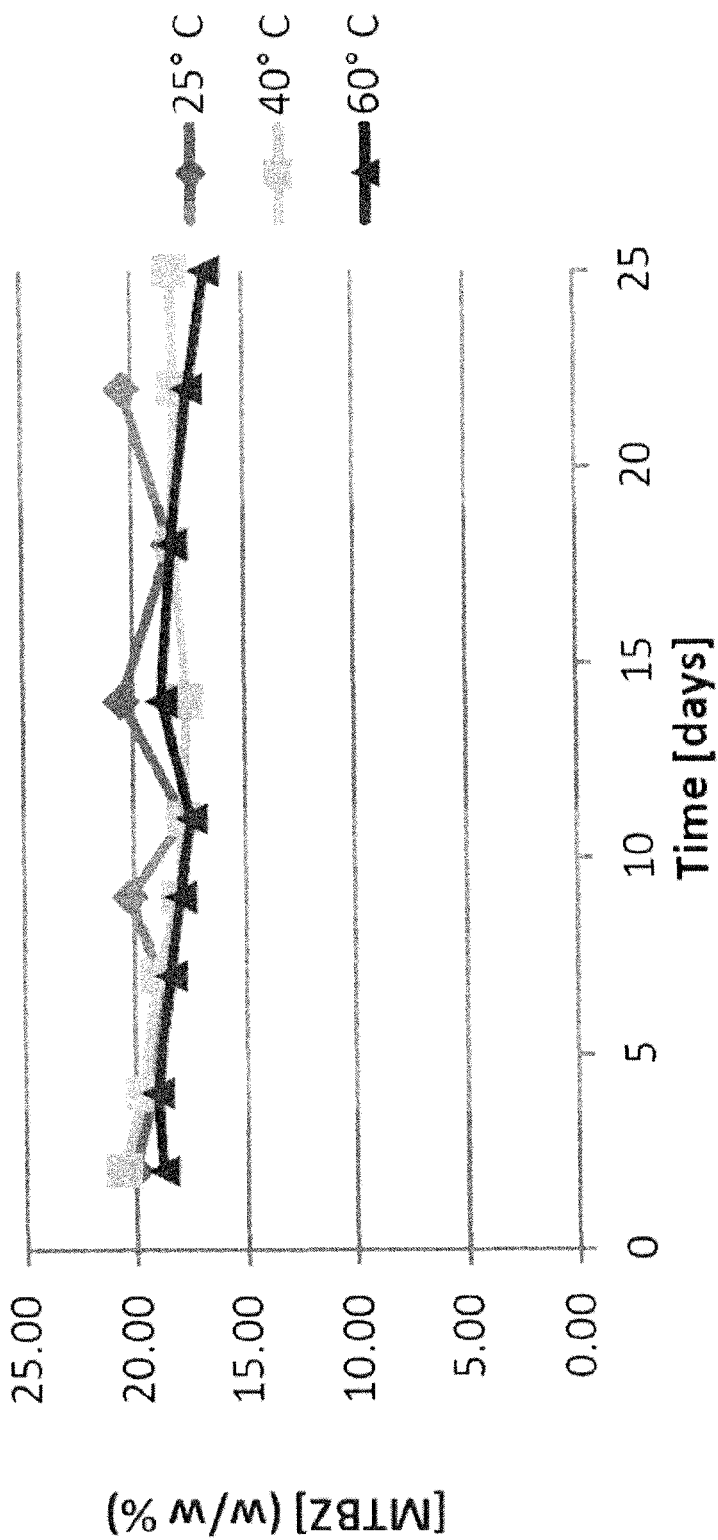
FIG. 4 shows the results of the stability tests conducted in example 2 with FCC particles having a drug load of 20%.
Figure 5:
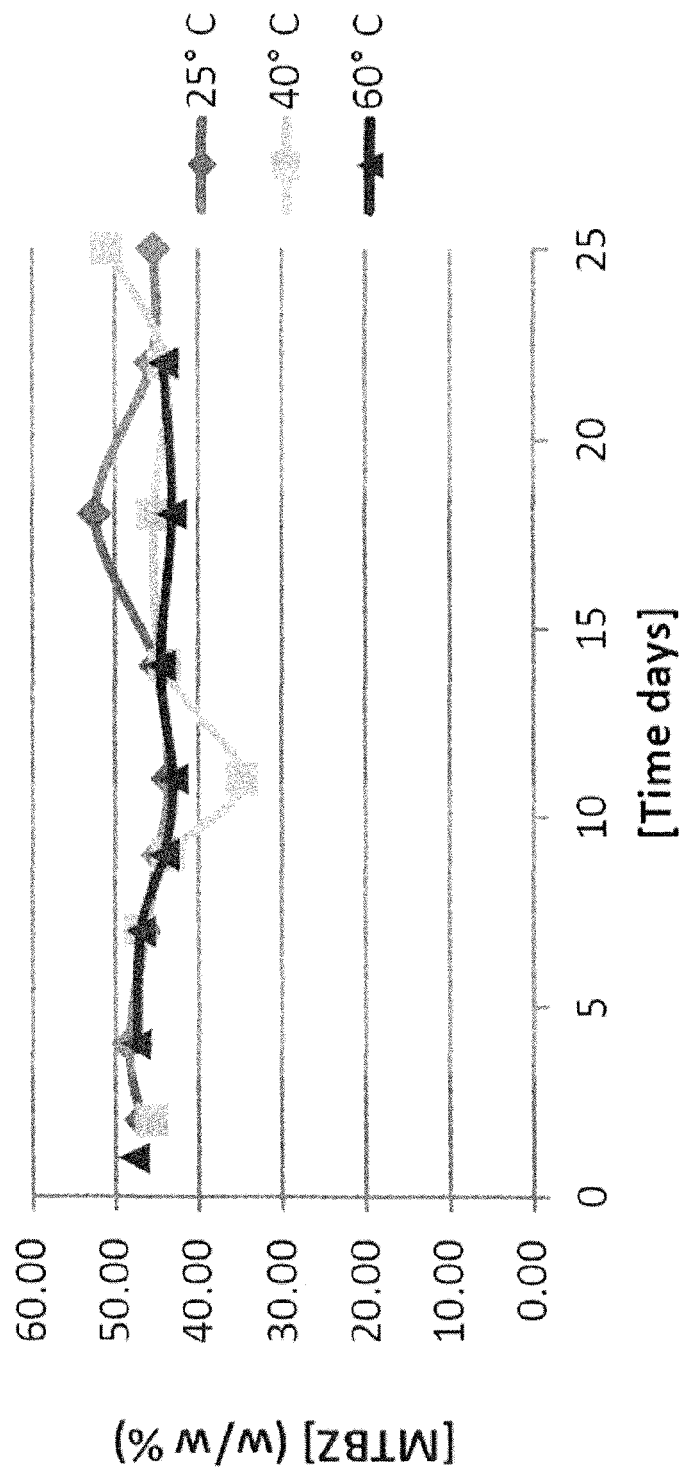
FIG. 5 shows the results of the stability tests conducted in example 2 with FCC particles having a drug load of 50%.

FIG. 4 shows the remaining MBZ content in % of the total powder mass. The results from HPLC-UV quantification showed deviation during the evaluation period, but were close to the theoretical drug load of 20%. The same pattern could be observed for FCC with a theoretical drug load of 50% (FIG. 5). MBZ content was fluctuating during the stability testing, but the average drug content remained almost constant.

EXAMPLE 3

3.1 Surface Modification

Method M1: Stearinisation in Aqueous Solution 5 g FCC S03 was mixed in a round-bottom flask with 100 ml degassed water. This slurry was heated up to 100° C. In a second round-bottom flask 1 g stearic acid (e.g. 200 mg stearic acid per gram FCC) and 20 ml water were heated to 100° C. Two drops of 1 molar NaOH were added to improve the solvation. The solution was then added to the first flask. This mixture was kept at given temperature for one hour. In order to prevent evaporation of the solvent a reflux condenser was applied. After 15 minutes, a massive amount of foam was formed, filling the flask. As it evidently prevented the FCC in the foam from further reacting with the solution, the flask was removed from the reflux condenser and swiveled thorough until the foam collapsed. This procedure was repeated every 15 minutes.

After an hour, the liquid was carefully poured off. The foam, that did not show any signs of wetness, was dried at 100° C. overnight to remove possibly trapped solvent from the pores.

Method M2: Stearinisation in 50% Ethanol-Water (FCC 200-Mod)

The solvent was changed to a mixture of 50% ethanol and 50% degassed water. The procedure was the same as in case of aqueous solution (M1). The reaction temperature was 83° C. conditioned by the temperature plateau of the solvent mixture.

3.2 Drug Loading

In this method, carbamazepine was dissolved in 50 ml ethanol and 0.5 g of FCC 200Mod was added. The mixture was then stirred for twenty minutes. Afterwards the loaded particles were separated from the solvent with a Büchner funnel and dried overnight in the vacuum drier at 40° C.

Figure 6:
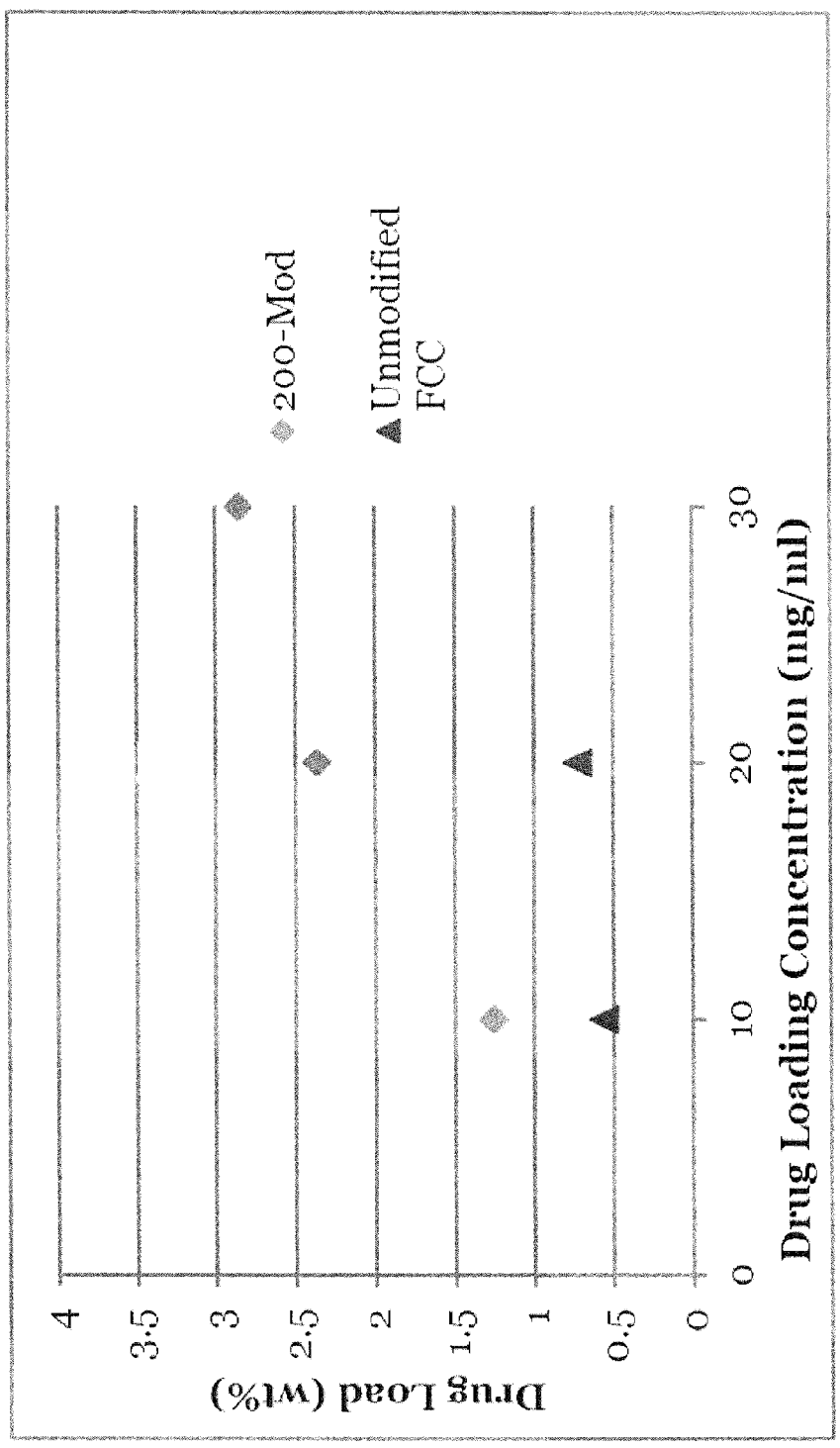
FIG. 6 shows the difference in drug loading capacity between modified and unmodified FCC.

The difference in drug loading capacity between modified and unmodified FCC is shown in FIG. 6. The ratio of drug load in unmodified FCC and 200-Mod is 1:3 at 20 mg/ml.

What is claimed:

1. A delayed release pharmaceutical formulation for delivering an active agent to the intestine, wherein said formulation comprises carrier particles and at least one active agent associated with the carrier particles, further wherein the carrier particles are porous particles that are surrounded by a material for colon targeting, further wherein the carrier particles comprise functionalized calcium carbonate, further wherein (a) the material for colon targeting comprises a compound which is susceptible to attack by colonic bacteria, and/or (b) the carrier particles are at least partially coated with either or both of a mucoadhesive compound and a sustained release coating.

2. The delayed release pharmaceutical formulation according to claim 1, wherein the functionalized calcium carbonate is a surface reacted calcium carbonate that is obtained by reacting natural or synthetic calcium carbonate with carbon dioxide and one or more acids, further wherein the carbon dioxide is formed in situ by the acid treatment and/or is supplied from an external source.

3. The delayed release pharmaceutical formulation according to claim 1, wherein the at least one active agent is adsorbed onto and/or absorbed into the carrier particles.

4. The delayed release pharmaceutical formulation according to claim 1, wherein the carrier particles are associated with at least 15% by weight of the at least one active agent based on the total weight of the carrier particles including the weight of the at least one active agent.

5. The delayed release pharmaceutical formulation according to claim 1, wherein the at least one active agent is selected from the group consisting of anti-inflammatory agents, anti-infective agents, immunomodulators and antibodies.

6. The delayed release pharmaceutical formulation according to claim 1, wherein the at least one active agent is (a) an anti-inflammatory agent selected from the group consisting of steroids, corticosteroids, non-steroidal anti-inflammatory agents, and herbal anti-inflammatory agents, or (b) an antibiotic, a virustatic, an antimycotic, an anthelmintic or an agent against other micro-organisms.

7. The delayed release pharmaceutical formulation according to claim 1, wherein the carrier particles are surrounded by a coating of the material for colon targeting.

8. The delayed release pharmaceutical formulation according to claim 1, wherein the carrier particles are within a matrix of the material for colon targeting.

9. The delayed release pharmaceutical formulation according to claim 1, wherein the material for intestinal targeting comprises a compound that is insoluble in the intestinal juice at a pH below 5 and that is soluble in the intestinal juice at a pH at or above 5.

10. The delayed release pharmaceutical formulation according to claim 1, wherein the carrier particles are at least partially coated with a compound that imparts hydrophobicity or hydrophilicity to the surface of the carrier particles.

11. The delayed release pharmaceutical formulation according to claim 1, wherein the carrier particles are associated with at least 20% by weight of the at least one active agent based on the total weight of the carrier particles including the weight of the at least one active agent.

12. A method of preparing a delayed release pharmaceutical formulation according to claim 1, said method comprising the steps of: (a) loading the porous carrier particles with the at least one active agent to obtain loaded carrier particles and (b) surrounding the loaded carrier particles with a material for colon targeting.

13. A method of treating gastrointestinal disorders comprising the step of administering to a subject in need thereof an effective amount of a delayed release pharmaceutical formulation according to claim 1.

* * * * *